United States Patent [19]

Bauer et al.

[11] Patent Number: 5,338,772
[45] Date of Patent: Aug. 16, 1994

[54] IMPLANT MATERIAL

[75] Inventors: Hans-Jörg Bauer, Flomborn; Gerd Bauer, Kleinostheim; Elvira Dingeldein, Dreieich; Helmut Wahlig, Darmstadt, all of Fed. Rep. of Germany

[73] Assignee: Merck Patent Gesellschaft mit beschrankter Haftung, Darmstadt, Fed. Rep. of Germany

[21] Appl. No.: 901,481

[22] Filed: Jun. 22, 1992

[30] Foreign Application Priority Data

Jun. 20, 1991 [DE] Fed. Rep. of Germany ....... 4120325

[51] Int. Cl.$^5$ ............................. A61F 2/00; B32B 3/26
[52] U.S. Cl. ................................... 523/115; 524/415; 524/417; 428/304.4; 428/330
[58] Field of Search ............... 523/115, 116; 524/415, 524/417; 428/330, 304.4

[56] References Cited

U.S. PATENT DOCUMENTS

| | | | |
|---|---|---|---|
| 4,610,692 | 9/1986 | Eitenmuller et al. | 523/116 |
| 4,843,112 | 6/1989 | Gerhardt et al. | 524/417 |
| 4,849,285 | 7/1989 | Dillon | 428/330 |

Primary Examiner—Paul R. Michl
Assistant Examiner—LaVonda DeWitt
Attorney, Agent, or Firm—Millen, White, Zelano & Branigan

[57] ABSTRACT

The invention relates to an implant material which is based on a composite material of calcium phosphate ceramic particles and bioabsorbable polymer, in which the proportion of calcium phosphate ceramic particles is at least 50% by weight and the particles are joined to one another by polymer bridges to give a three-dimensional open-pore structure in which the particle surfaces are covered with polymer to the extent of not more than 50%. This implant material is distinguished by particularly favorable growing-in and healing-in properties.

19 Claims, No Drawings

IMPLANT MATERIAL

SUMMARY OF THE INVENTION

The invention relates to an implant material which is based on a composite material of calcium phosphate ceramic particles and bioabsorbable polymer and is distinguished by particularly favorable growing-in and healing-in properties.

An efficient medical implant material for bone replacement must meet the requirement that it has a high mechanical stability. Mineral-based implant materials usually ensure a high mechanical stability only if they are employed as ceramics, that is to say therefore in the form of materials or workpieces sintered at sufficiently high temperatures.

Those implant materials which have a high bioactivity, that is to say to the extent that they are accepted by the organism and are integrated into it, are regarded as being particularly favorable for the healing-in process. In the case of bone replacement material, this means that it should soon fuse firmly and permanently with endogenous tissue, in particular with the bone.

Bone replacement materials based on calcium phosphate ceramics are bioactive on the basis of their being related chemically to the mineral phase of natural bone. The mineral phase of natural bone consists mainly of hydroxyapatite, a calcium phosphate having the empirical formula $Ca_5(PO_4)_3OH$.

Hydroxyapatite of synthetic or organic origin, for example from natural bone material, is therefore a raw material which is often used for the production of implants for bone replacement. Hydroxyapatite ceramic is essentially not absorbable in the organism. That is to say, the exogenous material is retained in practically unchanged form for a long period of time and integration into the organism takes place essentially by fusion with existing and regenerating bone and growing into the surrounding tissue.

From experience, the strength of the fusion of compact calcium phosphate ceramic with existing bone is mainly unsatisfactory. More favorable growing-in properties are shown by porous calcium phosphate ceramics.

Materials based on natural bone, which is mineralized by various treatments and converted into a ceramic system, it being necessary to retain the structure of bone as far as possible, are particularly favorable here. The processes have the common feature of removal of the organic bone constituents and subsequent compaction to the ceramic by sintering at appropriate temperatures. The organic contents are removed by chemical solution processes or by pyrolytic processes.

Because they correspond excellently with the pore system of natural bone, ceramic bone implants have considerable biological advantages in their growing-in properties and healing in the organism.

Shaped articles of ceramic material, in particular of the abovementioned type, are primarily employed for replacing load-bearing bone structures which must withstand high mechanical stresses. Examples of these are bone prostheses and bone-joining elements, such as, for example, intra medullary nails, bone screws and osteosynthesis plates.

Composite materials based on ceramic particles and physiologically tolerated polymer are gaining increasing importance for replacement of bone structures subjected to only little stress, if any, such as, for example, for filling spongiosa bone defects following surgery or accidents, for filling tooth extraction cavities or for plastic surgery treatment of contour defects in the maxillo-facial region. It is mainly of interest in the case of such materials that they can easily be subjected to shaping, for example by simple mechanical working or by plastic deformation, before or during the operation.

Composite materials which are prepared from ceramic shaped articles and polymer and should be close to natural bone in their mechanical and biological properties are also of interest for the production of implants having load-bearing functions.

Composite materials of the type described, including in particular those based on calcium phosphate particles and bioabsorbable polymer, are known per se.

WO 90/01342 describes implant materials which consist of finely divided or granular ceramic particles which are compatible with the body, in particular of hydroxyapatite of inorganic origin, mixed with lower hydroxycarboxylic acid oligomers or polymers which are absorbable by the body, in particular specifically modified lactide/glycolide polymers. The resulting composite materials are compact to porous and rigid to plastically deformable, depending on how these starting components are chosen and the mixing ratios adjusted. An essential common feature is, however, that the polymer forms a closed phase in which the ceramic particles are dispersed or by which the particles are at least enclosed completely.

WO 90/01955 describes a composite material which consists of mineralized bone material impregnated with an absorbable biocompatible macromolecular material such that at least the surface of the mineral phase is covered.

DE 3134728 describes a material for bone implants which consists of granular tricalcium phosphate ceramic impregnated with a broad spectrum microbicide and covered or coated with a biocompatible organic material.

DE 2742128 describes a solid, non-porous bone replacement material which essentially consists of a biologically compatible polymer to which an inorganic filler has been added. The organic polymers disclosed are those based on hydroxycarboxylic acids and the fillers disclosed are calcium phosphates. The polymer is evidently also present in this material as a continuous phase in which inorganic particles are embedded.

In the materials according to DE 2620891, sintered calcium phosphates are combined with biodegradable polymer. Although no further details are given, it is to be assumed that the inorganic component in the materials described is essentially always enclosed, covered or coated by polymer.

Although the composite materials of the type described have favorable mechanical and biological properties, they are nevertheless still in need of improvement. In fact, more precise clinical studies have shown that in the healing-in process following implantation, initially only connective tissue is preferentially regenerated in the contact region with the polymer material. In contrast, the open mineral contact surfaces of implants comprising only calcium phosphate ceramic stimulate the preferred regeneration of mineral bone matrix. Since in the known composite materials the mineral component is essentially always coated by polymer, it is not a direct growing-on and growing-in of regenerated mineral bone matrix which takes place, as is desirable, but mainly an embedding in connective tissue. In the end, this results in an only inadequate mechanical strength of the transition from implant to endogenous bone substance.

An object of the invention is to provide an improved composite material for bone replacement, which has particularly favorable growing-in and healing-in properties coupled with at least equally good overall properties in respect of mechanical strength, workability and bioactivity.

Upon further study of the specification and appended claims, further objects and advantages of this invention will become apparent to those skilled in the art.

It has now been found that this is achieved with an implant material which is based on a composite material of calcium phosphate ceramic particles and bioabsorbable polymer, in which the proportion of calcium phosphate ceramic particles is at least 50% by weight and the particles are joined to one another by polymer bridges to give a three-dimensional, open-pore structure in which the particle surfaces are covered with polymer to the extent of not more than 50%. It has been found that, because of the presence of calcium phosphate ceramic particles having a high proportion of free surface not covered with polymer in association with the three-dimensional, open-pore structure formed by polymer bridges, the regeneration of mineral bone matrix and therefore a particularly strong and intimate fusion with the endogenous bone substance takes place to an unexpectedly high degree in the composite material according to the invention.

The implant material according to the invention can be prepared in a simple manner by heating a mixture of the components by means of microwave radiation. In this procedure, the polymer which melts and then solidifies again forms with the calcium phosphate ceramic particles a three-dimensional, open-pore structure in which the ceramic particles are joined to one another by polymer bridges. With a proportion of ceramic particles of at least 50% by weight and the joint which develops via polymer bridges, it is ensured that the particle surfaces are covered with polymer to the extent of not more than 50%. A property of the implant material according to the invention which is very favorable for use in practice is that after renewed heating with microwave radiation it can be deformed plastically without the structure of the material changing during this operation.

The invention thus relates to an implant material based on a composite material of calcium phosphate ceramic particles and bioabsorbable polymer, which is characterized in that the proportion of calcium phosphate ceramic particles in the material is at least 50% by weight and the particles are joined to one another by polymer bridges to give a three-dimensional, open-pore structure in which the particle surfaces are covered with polymer to the extent of not more than 50%.

The invention furthermore relates to a process for the preparation of such an implant material by heating a mixture of the components, in which the proportion of calcium phosphate ceramic particles is at least 50% by weight, by means of microwave radiation.

The invention finally relates to a process for shaping such an implant material, in which this is heated to plastic deformability by means of microwave radiation and is then deformed mechanically.

Starting components which can be employed for the implant material according to the invention are in principle all the calcium phosphate ceramic materials and bioabsorbable polymer materials known in the relevant field.

Appropriate ceramic materials are essentially to be understood as those in which the calcium phosphate on which they are based has a Ca:P ratio of between 1.0 and 2.0 and which have been sintered to form the ceramic at a sufficiently high temperature, as a rule in the range of about 800°–1500° C. The calcium phosphates on which they are based can be of synthetic origin, for example from the reaction of calcium oxide with phosphoric acid in the appropriate molar ratio, or of natural origin, for example from a mineral or organic source. Typical calcium phosphates are hydroxyapatite, tricalcium phosphate and tetracalcium phosphate and conversion and modification products thereof, which can also be present side by side as mixed phases in the ceramic. Calcium phosphates of organic origin, in particular hydroxyapatite from natural bone, are preferred. The latter can be obtained from bone by mineralization by methods which are known per se.

The calcium phosphate ceramic particles for the composite material according to the invention can be employed in powder to granule form, it being possible for any particle size of about 20 μm–5 mm to be chosen. Granules having particle sizes of 0.1–3 mm, in particular 0.5–1.5 mm, are particularly preferred.

The particles can be compact, that is to say of low porosity, or porous. The former chiefly applies in the case of pulverulent materials, and the latter is preferably realized in the case of granules.

A porosity of up to 90% of the particle volume can be present in porous materials, an open porosity being preferred. The materials can have a microporosity with pore sizes of between 1 and 100 μm and/or a macroporosity with pore sizes of up to about 3 mm, depending on their origin and particle size.

Because they correspond particularly well with natural bone in respect of chemical composition, crystallite and pore structure, bone ceramic particles are particularly favorable as the ceramic component in the composite material according to the invention. The bone ceramic particles are typically used in the form of highly porous spongiosa granules or in the form of corticalis granules, which have a low porosity. These materials and their preparation, modification, processing and use are familiar to the expert or can be found without problems in the relevant technical literature, such as, for example, the specifications cited in the introduction.

Possible bioabsorbable polymers are synthetic polymers and naturally occurring, high molecular weight materials, which can also be modified chemically in a known manner. Typical naturally occurring, high molecular weight substances are polysaccharides, such as starch, cellulose and derivatives thereof, proteins, such as gelatin and collagen, or triglycerides of higher alkanecarboxylic acids, such as high-melting fats and waxes. Typical synthetic polymers are chiefly oligomers and polymeric esters of hydroxycarboxylic acids, such as, in particular, of lactic acid and glycolic acid. These materials and their preparation, modification, processing and use are also familiar to the expert or can be found without problems in the relevant technical literature. The specifications cited in the introduction and the literature referred to therein may again serve as a reference. Particularly preferred polymer components in the composite material according to the invention are polymer materials based on polylactides and/or polyglycolides. These materials can be homopolymers of D-, L- and D,L-lactic acid and of glycolic acid, copolymers or mixtures thereof and mixtures with corresponding oligomers and monomers. The consistency of the polymer material can be adjusted between brittle-hard, flexible-elastic and tenacious-viscous, depending on the choice of the chemical composition, of the degree of polymerization, of the proportion of oligomers and monomers or of other customary modifications and additions. The average molecular weight of the polymer material is advantageously about 200–10,000 and preferably about 1,000–3,000. The polymer material should advantageously be fusible in a temperature range which does not extend beyond 180° C. The polymer is ideally chosen or adjusted so that it is of essentially hard consistency at room temperature but softens at temperatures between about 40° and 60° C. to the extent that it becomes plastically deformable.

A decisive feature of the composite material according to the invention is the three-dimensionally open-pore structure, which is constructed such that the calcium phosphate ceramic particles are joined to one another by polymer bridges, the particle surfaces being covered with polymer to the extent of not more than 50%.

The pore size of the composite material can be up to about 3 mm, and is preferably in the range of about 0.01–1 mm.

An essential precondition for the formation of such a structure is that the proportion of calcium phosphate ceramic particles in the composite material is at least 50% by weight. The proportion of calcium phosphate ceramic particles is preferably 75–95% by weight. 98% by weight is to be set as the upper limit for a material with a still usable cohesion. The ratio of ceramic particles to polymer can be optimized depending on the nature of the components, in particular on the porosity of the particles. It is thus particularly favorable in the case of highly porous spongiosa ceramic granules to provide not more than a maximum of 80% by weight, since a certain proportion of polymer is absorbed by the porous material. In the case of corticalis ceramic particles of low porosity, the chosen proportion can be higher, but not more than 90% by weight.

Another essential precondition for the formation of the structure is the nature of the preparation of the composite material by heating an appropriate mixture of the components by means of microwave energy. This causes rapid melting of the polymer material, during which many individual separate drop-like polymer domains which do not flow together and which join the ceramic particles to a three-dimensional network with a bridge-like linkage are formed under intrinsic forces of cohesion. It is assumed that this formation of the bridge-like linkage is caused by a selective and sudden heating of the polymer material, which acts simultaneously in the entire volume, by the microwave energy, while the ceramic particles essentially do not heat up. For this reason, the heating time chosen can also be relatively short. Because of the penetrating character of microwave energy, the heating time is also largely independent of the amount and volume of the material mixture, and at all events of the microwave power. The microwave power to be irradiated is advantageously to be adjusted primarily to the melting temperature range of the polymer. Possible sources of microwave energy are microwave ovens such as are customary in the domestic sector. These usually operate at a frequency of 2.45 GHz at a power of between 450 and 1000 watt. The treatment time of the material using such appliances is in the minute range, typically between 2 and 10 minutes, depending on the microwave power set. The corresponding operating conditions can otherwise be determined and optimized for the individual case without problems by simple routine experiments.

To prepare the composite material according to the invention in practice, the components comprising calcium phosphate ceramic particles and polymer material are first mixed intimately in the desired ratio. The polymer material can be in the form of a powder, granules or a plastic-pasty composition, depending on its nature. Thorough mixing is carried out with the methods and apparatuses appropriate for the particular materials. The mixture is then advantageously brought into a shaping vessel made of an inert microwave-resistant material. The shaping can be adjusted to the later use of the implant. However, it is also possible merely to form blanks, from which shaped implant articles corresponding to the particular intended use can then be worked later. The composite material according to the invention having the structure already described is formed by treatment with microwave energy in a commercially available apparatus at, for example, 450 watt for a period of 3–5 minutes. The cooled composite material has a stable structure and can be stored without problems.

In individual cases it is indeed also possible, by empirical choice of starting components and mixing ratios, to formulate compositions which can also be processed to a composite material of comparable structure by supplying the required heat energy using other heat sources, such as, for example, conventional ovens or infrared lamps. However, control of the heat supply overall is extremely critical here, and as a rule complete fusion of the polymer material occurs, leading to substantial to complete coating or enclosure of the ceramic particles by the polymer. According to the invention, however, only heating by means of microwaves has proved to be a reliable method which extends over the entire range of compositions and all the variants of the starting materials.

The material can be shaped by various measures, depending on the consistency established. Materials having a mainly firm consistency can be worked by mechanical means, such as sawing, cutting, filing and milling with tools customary for this purpose. Materials which have been formulated in a more plastic-flexible consistency can also be shaped by mechanical pressure. Materials which are formulated such that they are solid at room or body temperature and soften to plastic deformability by gentle heating are particularly advantageous. The use of microwave energy is again particularly favorable for this heating step. In this way, analogously to the preparation process, it is reliably ensured that the three-dimensional, open-pore network structure formed in the material by polymer bridges and the substantial absence of polymer on the ceramic particle surfaces are retained. Such composite materials which can be plasticized by microwave energy can be deformed by mechanical pressure and in this way adjusted well to the local circumstances at the site of implantation, for example in the case of filling of spongiosa bone defects, cyst cavities and tooth extraction cavities and in joining or replacing bone fragments. The deformability is as a rule retained for a period suitable for processing, which is in the minute range. After cooling, the material again has its original firm consistency.

The composite material according to the invention is especially suitable as an implant material for bone replacement since, as is found in model clinical experiments, it is distinguished by particularly favorable growing-in and healing-in properties. This lies evidently in the unique structural features which the materials of comparable composition from the prior art do not have.

The three-dimensional open-pore structure, which particularly corresponds to the structure of natural spongy bone substance, promotes inshoots of regenerating bone tissue, an intimate joint with the implant developing.

The advantages of bioabsorbable polymer materials and of calcium phosphate ceramic in implants are generally recognized per se. The high proportion of exposed surface of the calcium phosphate ceramic particles of at least 50% and preferably 75–95% promotes the preferred regeneration and growth of endogenous mineral bone substance with reduced regeneration of connective tissue.

The composite material according to the invention has many uses as an implant material for bone replacement. Depending on the strength and mechanical stress resistance of the material, prefabricated shaped implant articles, for example for the replacement of defined bone parts, can be produced therefrom, or the material can be used for filling bone cavities and for reconstituting bone regions which are not load-bearing.

The latter field of use is a preferred field of use of the composite material according to the invention. Of chief importance here are the filling of tooth extraction cavities, the reconstitution of contour defects in the maxillofacial region and the filling of spongiosa bone defects following disease-related surgery or in the case of accident surgery.

Pharmaceutical active compounds such as are known and customary for the corresponding uses can also be incorporated into the composite materials according to the invention. For example, antibiotic and/or cytostatic pharmaceuticals for suppressing or combating infections or for cancer therapy are advantageous. Active compounds which promote the healing-in process, such as, for example, agents which promote cell, vessel and bone growth, can furthermore be employed. Correspondingly active peptide growth factors, vitamins and hormones, for example, are suitable. It is advantageous for the active compound to be employed or the active compound combination first to be incorporated into the polymer material in the appropriate dosage and then to prepare the composite material according to the invention from this material.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications cited above and of corresponding German application P 41 20 325.9, are hereby incorporated by reference.

EXAMPLE 75 parts by weight of granules of spongiosa bone ceramic having a particle size of 0.5–1.25 mm are intimately mixed successively with 22 parts by weight of poly-(D,L)--lactide having a molecular weight of 2000 and with 3 parts by weight of (D,L)-lactic acid. The composition is introduced into a Teflon-coated mold and compacted with gentle pressure on the surface. The filled mold is placed off-center in a commercially available microwave apparatus with a rotating plate and treated with an energy of 450 watt for 3.5 minutes. After removal, the material is allowed to cool in the absence of moisture. A firm, open-pore implant material in which the ceramic granules are joined by polymer bridges is obtained. About 80% of the granule surface is not covered by polymer.

By renewed microwave treatment, the material becomes plastically deformable for a period of about 3 minutes, and then solidifies again.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An implant material comprising a composite material containing calcium phosphate ceramic particles and bioabsorbable polymer, wherein the proportion of calcium phosphate ceramic particles in the material is at least 50% by weight and said particles are joined to one another by polymer bridges, thereby defining a three-dimensional open-pore structure in which the particle surfaces are covered with polymer to the extent of not more than 50%.

2. An implant material according to claim 1, wherein said composite material contains at least 50 wt. % and not more than 98 wt. % of said particles.

3. An implant material according to claim 2, wherein said ceramic particles are made of sintered bone and said polymer is based on polylactides and/or polyglycolides.

4. An implant material according to claim 3, wherein said bone ceramic particles are porous.

5. An implant material according to claim 4, wherein the porous bone ceramic particles have an open porosity.

6. An implant material according to claim 5, wherein said composite contains sintered spongiosa granules as said porous bone ceramic particles.

7. An implant material according to claim 6, wherein said composite contains not more than 80% by weight of particles.

8. An implant material according to claim 3, wherein said bone ceramic particles have a low porosity.

9. An implant material according to claim 8, wherein said composite contains sintered corticalis granules as said bone ceramic particles.

10. An implant material according to claim 9, wherein said composite contains not more than 90% by weight of particles.

11. An implant material according to claim 2, wherein said composite further contains one or more pharmaceutically active compounds.

12. An implant material according to claim 2, wherein said composite is a composite material obtained by heating a mixture of said ceramic particles and bioabsorbable polymer by means of microwave radiation.

13. An implant material according to claim 2, wherein said particles have a particle size of 20 μm–5 mm.

14. An implant material according to claim 2, wherein said polymer has an average molecular weight of 200–10,000.

15. An implant material according to claim 2, wherein the pore size of said composite is 0.01–1 mm.

16. An implant material according to claim 2, wherein said composite contains 75–95% by weight of said particles.

17. A process for the preparation of an implant material based on a composite material of calcium phosphate ceramic particles and bioabsorbable polymer wherein the particles are joined to one another by polymer bridges to give a three-dimensionally open-pore structure in which the particle surfaces are covered with polymer to the extent of not more than 50%, said process comprising heating by means of microwave radiation a mixture of said ceramic particles and bioabsorbable polymer, wherein the proportion of calcium phosphate ceramic particles is at least 50% by weight.

18. A process according to claim 17, wherein said ceramic particles are sintered bone ceramic particles and said polymer is based on polylactides and/or polyglycolides.

19. In a process for shaping an implant material, the improvement wherein an implant material according to claim 2 is heated to plastic deformability by means of microwave radiation and is then deformed by mechanical pressure.

* * * * *